(12) United States Patent
Brockman et al.

(10) Patent No.: US 8,919,356 B2
(45) Date of Patent: Dec. 30, 2014

(54) OZONE GENERATION MODULE

(75) Inventors: Irene M. Brockman, Cambridge, MA (US); Steven J. Kuehl, Stevensville, MI (US); Mark M. Senninger, Saint Joseph, MI (US)

(73) Assignee: Whirlpool Corporation, Benton Harbor, MI (US)

( * ) Notice: Subject to any disclaimer, the term of this patent is extended or adjusted under 35 U.S.C. 154(b) by 789 days.

(21) Appl. No.: 12/967,134

(22) Filed: Dec. 14, 2010

(65) Prior Publication Data

US 2012/0145198 A1    Jun. 14, 2012

(51) Int. Cl.
*B08B 3/00* (2006.01)
*C02F 1/78* (2006.01)
*A61L 2/18* (2006.01)

(52) U.S. Cl.
CPC . *C02F 1/78* (2013.01); *A61L 2/183* (2013.01); *A61L 2/186* (2013.01); *A61L 2202/122* (2013.01); *A61L 2202/15* (2013.01); *A61L 2202/24* (2013.01); *C02F 2201/782* (2013.01); *C02F 2307/12* (2013.01)
USPC ............... 134/60; 68/13 R; 68/5 C; 68/12.02; 68/207; 134/10; 134/26; 134/109; 134/18; 8/158; 8/137

(58) Field of Classification Search
CPC .... D06F 35/001; C02F 1/78; C02F 2201/782; C01B 13/10; B08B 2203/005
USPC ......... 134/31, 115 R; 68/12.01, 12.02, 12.12, 68/13 R, 19; 8/147, 148
See application file for complete search history.

(56) References Cited

U.S. PATENT DOCUMENTS

| 5,666,949 A | 9/1997 | Debe et al. |
| 6,620,210 B2 * | 9/2003 | Murphy et al. ................ 8/149.1 |
| 6,746,580 B2 | 6/2004 | Andrews et al. |

(Continued)

FOREIGN PATENT DOCUMENTS

| DE | 89 07 023 U1 | 10/1990 |
| DE | 100 60 478 A1 | 6/2002 |

(Continued)

OTHER PUBLICATIONS

Tatapudi et al., May 1994, Simultaneous Synthesis of Ozone and Hydrogen Peroxide in a Proton-Exchange-Membrane Electrochemical Reactor, The Electrochemical Society, vol. 141.*

(Continued)

*Primary Examiner* — Michael Barr
*Assistant Examiner* — Thomas Bucci

(57) ABSTRACT

An ozone supply module for supplying ozonated water to an appliance that typically includes: an appliance module housing having a water inlet; a water outlet; and an electrical connection for receiving electrical power; a proton exchange membrane cell positioned within the housing; and a water conveying system within the module housing and operably connected to both the water inlet and water outlet. The water conveying system is typically configured to allow water to flow through the deionizing resin and into contact with the proton exchange membrane cell. The module and the proton exchange membrane cell receive electrical power from a home appliance when the module is operably connected to the appliance. The module produces water that contains (dissolved) ozone to be delivered to a chamber within the appliance when the module is in the engaged position with the appliance. The appliance is typically a residential appliance.

18 Claims, 11 Drawing Sheets

(56) References Cited

U.S. PATENT DOCUMENTS

| | | |
|---|---|---|
| 6,967,008 B1 | 11/2005 | Barnes |
| 7,275,400 B2 | 10/2007 | Severns et al. |
| 7,413,637 B2 | 8/2008 | Scheper et al. |
| 7,438,732 B2 | 10/2008 | Shurtleff et al. |
| 7,655,460 B2 | 2/2010 | Rouleau et al. |
| 7,740,749 B2 | 6/2010 | Herrington et al. |
| 2002/0185423 A1* | 12/2002 | Boyd et al. ............ 210/167 |
| 2005/0204784 A1 | 9/2005 | Kirejczyk, III et al. |
| 2006/0037869 A1 | 2/2006 | Mitchke |
| 2007/0022789 A1 | 2/2007 | Heiligenmann et al. |
| 2007/0141210 A1 | 6/2007 | Kuzmier |
| 2007/0251549 A1 | 11/2007 | Heilgenmann et al. |
| 2007/0261723 A1 | 11/2007 | Price et al. |
| 2008/0102333 A1 | 5/2008 | Watanabe et al. |
| 2009/0039033 A1 | 2/2009 | Kee et al. |
| 2009/0255299 A1 | 10/2009 | Hiro et al. |
| 2010/0181208 A1* | 7/2010 | Denison et al. ............ 205/687 |

FOREIGN PATENT DOCUMENTS

| | | |
|---|---|---|
| DE | 102 20 315 A1 | 1/2003 |
| DE | 699 05 766 T2 | 9/2003 |
| DE | 103 41 194 A1 | 3/2005 |
| DE | 103 60 906 A1 | 7/2005 |
| JP | 4 089 023 A | 3/1992 |
| WO | 02/48054 A1 | 6/2002 |
| WO | WO 2005/054545 A1 | 6/2005 |
| WO | 2006/033762 A2 | 3/2006 |
| WO | 2008/150541 A1 | 12/2008 |

OTHER PUBLICATIONS

German Search Report dated Jul. 12, 2012 (German Publication No. DE 10 2011 054 483.6).

\* cited by examiner

OZONE GENERATION MODULE

SUMMARY OF THE INVENTION

An aspect of the present invention typically includes an ozone supply module for supplying ozonated water to an appliance that typically includes: an appliance module housing having a water inlet; a water outlet; and an electrical connection for receiving electrical power; a proton exchange membrane cell positioned within the housing; and a water conveying system within the module housing and operably connected to both the water inlet and water outlet. The water conveying system is typically configured to allow water to flow through a deionizing resin and into contact with the proton exchange membrane cell. The electrical connector typically allows the module to receive electrical power from an appliance, typically a residential home appliance, when the module is operably connected to an appliance and typically supplies electrical power to the proton exchange membrane cell. The ozone supply module is typically capable of being removably changed between being engaged and disengaged with the appliance. The ozone supply module produces water to be delivered to a chamber within the appliance when the module is in the engaged position with the appliance and the water leaving the module and being delivered to the appliance chamber contains dissolved ozone.

Another aspect of the present invention is generally directed toward an ozone supply module for supplying ozonated water to an appliance, typically for use by the appliance in connection with one or more functions provided by the appliance. The ozone supply module typically includes: an appliance module housing comprising: a water inlet; a water outlet; and an electrical connection for receiving electrical power; a proton exchange membrane cell positioned within the housing; and a water conveying system within the module housing and operably connected to both the water inlet and the water outlet and configured to allow water to flow into contact with the proton exchange membrane cell. The electrical connection typically allows the module to receive electrical power from an appliance when the module is operably connected to the appliance and typically supplies electrical power to the proton exchange membrane cell. The ozone supply module is typically capable of being removably changed between being engaged and disengaged with the appliance. The ozone supply module typically produces water to be delivered to a chamber within the appliance when the module is in the engaged position with the appliance and the water leaving the module and being delivered to the chamber includes dissolved ozone. Typically, the appliance is a residential home appliance.

Another aspect of the present invention includes an appliance system that includes: an appliance having a processing chamber and a module connection; and a removable ozone supply module capable of being engaged and disengaged with the module connection. The removable ozone supply module typically includes: a housing having an interior, a water inlet, a water outlet; an electrical connection; a proton exchange membrane cell positioned within the housing and operably connected to the electrical connection; and a water conveying system within the housing and operably connected to both the water inlet and the water outlet and configured to allow water to flow into contact with the proton exchange membrane cell such that the proton exchange membrane cell generates ozone. When the module is engaged to the appliance the module typically receives electrical power from the appliance and water flows through the water inlet, contacts and/or travels through the proton exchange membrane cell and thereafter leaves the module through the water outlet. The ozone supply module typically produces water to be delivered to the processing chamber within the home appliance when the module is engaged with the appliance and the water leaving the module and being delivered to the appliance chamber includes dissolved ozone. Typically, the appliance is a residential home appliance.

DETAILED DESCRIPTION OF THE DRAWINGS

DETAILED DESCRIPTION OF THE INVENTION

For purposes of description herein, the terms "upper," "lower," "right," "left," "rear," "front," "vertical," "horizontal," and derivatives thereof shall relate to the invention. However, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The present invention is generally directed toward an ozone supply module for supplying ozonated water to an appliance, an appliance system utilizing an ozone supply module and a method of treating an article, an interior surface of an appliance, or a substance within the appliance with an ozonated fluid. Typically, the appliance is a home or residential appliance. The appliance is typically not a commercial appliance, but conceivably could be.

Figure 1:
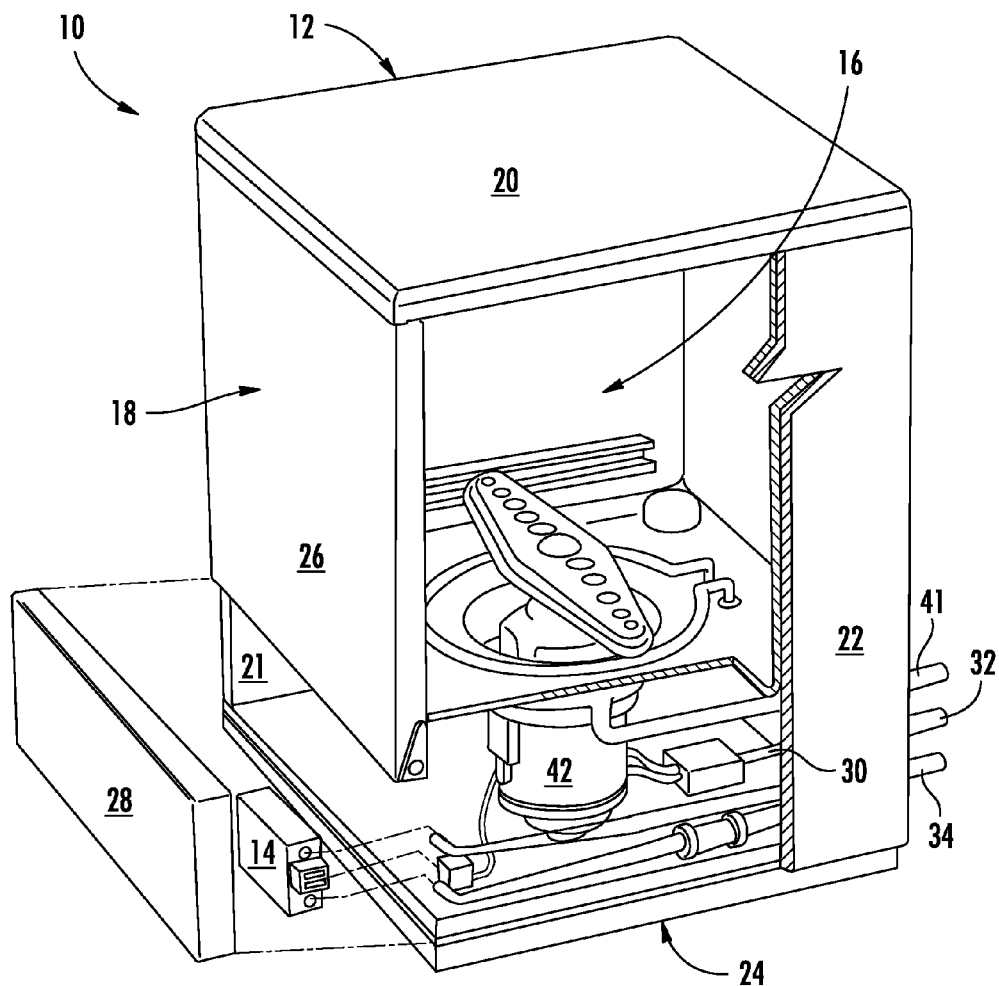
FIG. 1 is a perspective view of an embodiment of the present invention with a side of the appliance partially broken away to show various interior components of an appliance.

According to an aspect of the present invention, the appliance system 10 includes an appliance 12 and an ozone supply module 14, which supplies an ozonated fluid to the interior 16 of the appliance 12. The appliance typically has a front surface 18, a top surface 20, two side surfaces (the left side of the appliance 21 and the right side of the appliance 22 as shown in FIG. 1), and a bottom surface 24. On some appliances, the front surface 18 includes at least one door 26 typically hingedly connected to the sides of the appliance or an edge of an aperture within the front surface 18 of the appliance. For example, in the context of a front loading washer or dryer. A removable plate 28 may also be employed to cover and allow access to various components of the appliance including the ozone supply module 14 to allow for ready access and allow a user to remove the module 14 and replace it with a new module. The appliance 12 may be any household appliance (a dishwasher as shown in FIG. 1) such as a dishwasher, washer-dryer system or other commercial or household appliance, more typically a residential household appliance. The appliance is typically connected to an electrical source using an electrical connector 30. The appliance also is typically connected to at least one water source, more typically connected to a hot water source 32 and a cold water source 34.

The ozone supply module 14 typically contains all of the components within it to generate dissolved ozone. With reference to FIGS. 6-10, the module 14 typically has a water inlet and a water outlet (36 and 38) that are typically sealed using o-rings made of a resilient material with ozone resistance such as o-rings made of VITON™ by DuPont. VITON™ is a fluroelastomer with excellent heat resistance (up to about 400 F). The module also typically contains an electrical connection 40. The module 14 may have a rectangular cross-sectional geometry, but other cross-sectional geometrics such as a circular or oval cross-section may also be employed. A cuboid or cylindrical shape is most typically employed. The module 14 is typically at least about 1½ inches long and typically up to about 12 inches long. Typically, the diameter is at least about ½ inch in diameter and up to about 4 inches in diameter. The rectangular configuration is most typically cuboid to best accommodate the configuration of the proton exchange membrane(s). The module is typically designed to be ergonomic during both installation and use. The connection location for the module on the appliance is typically easily accessible by an end user of the appliance. Typically, the module can be accessed without moving the appliance from its location of normal use.

The appliance also typically includes at least one motor and optionally a plurality of motors 42. The motor or motors and the ozone module may all receive electrical power from the same electrical source. Alternatively, they may receive power from separate electrical sources. Additionally, the ozone supply module may not have an electrical connection where such a connection is not necessary. The appliance 12 may also include a water drain line 41.

Figure 2:
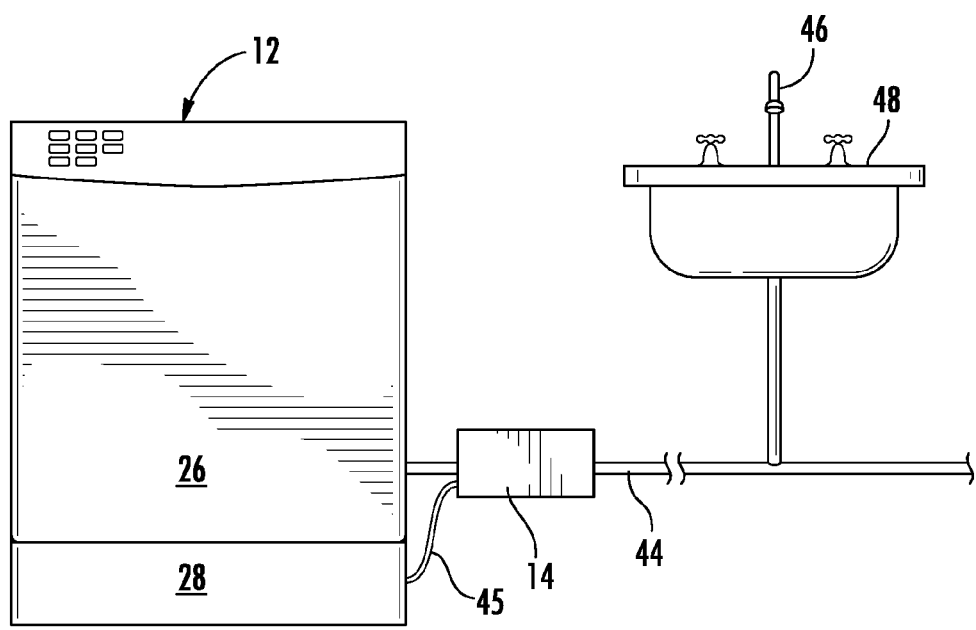
FIG. 2 is a Front elevational view of an appliance system incorporating an ozone module according to an aspect of the present invention.

As shown in FIG. 1, the ozone supply module may be a replaceable module located within the housing of appliance 12 typically behind an enclosure, door or panel that may be hingedly or frictionally connected to the appliance exterior, interior or other surface. Additionally, as shown in FIG. 2, the ozone supply module 14 may be placed outside of the appliance 12 and in line with a tap water or other fluid supply running through plumbing conduits 44. The ozone supply module may not contain an electrical connection or, when electrical power is necessary to power a portion of the ozone supply module 14, the electrical power may come directly from the appliance 12 via electrical wire 45 as shown in FIG. 2 or may be received directly from an electrical socket, typically a standard household electrical socket. FIG. 2 shows the ozone supply module in line with an overall plumbing system. The overall plumbing system, in this case, includes a faucet 46 and a sink 48.

Figure 3:
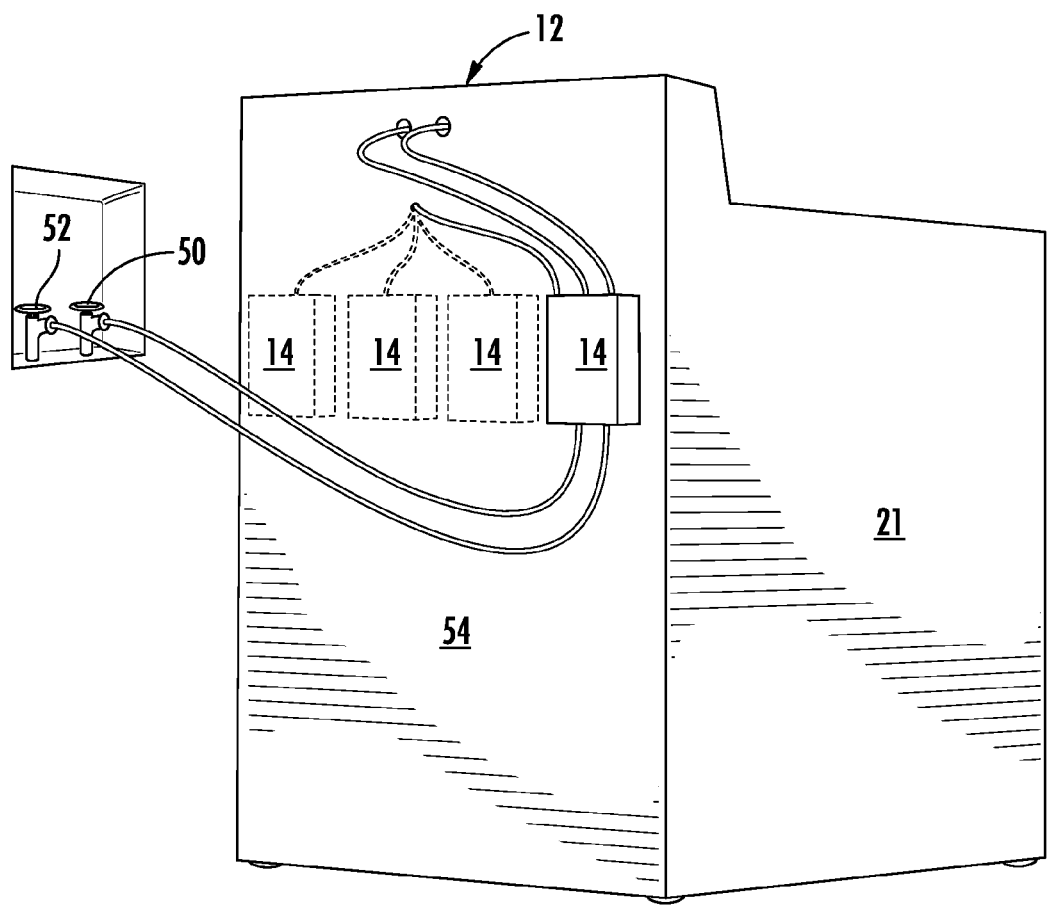
FIG. 3 is a rear perspective view of another embodiment of an appliance incorporating one or a plurality of ozone modules according to an aspect of the present invention.

As shown in FIG. 3, the ozone supply module of the present invention may receive water directly from a hot water supply faucet 50 and cold water supply faucet 52 or two different water sources. Because ozone degrades at higher temperatures, cold tap water (about 48 F to about 65 F) is preferably employed in connection with the various aspects of the present invention. When necessary for additional ozone production, multiple ozone supply modules may be used either in parallel or in series and the one or more modules may supply ozonated fluid to one or a plurality of different appliances, typically residential grade appliances for use in a home or other residence. The ozone supply modules 14 are shown in series in FIG. 3 and mounted to the rear 54 of an appliance 12 (a laundry appliance is shown in FIG. 3).

Figures 4, 5:
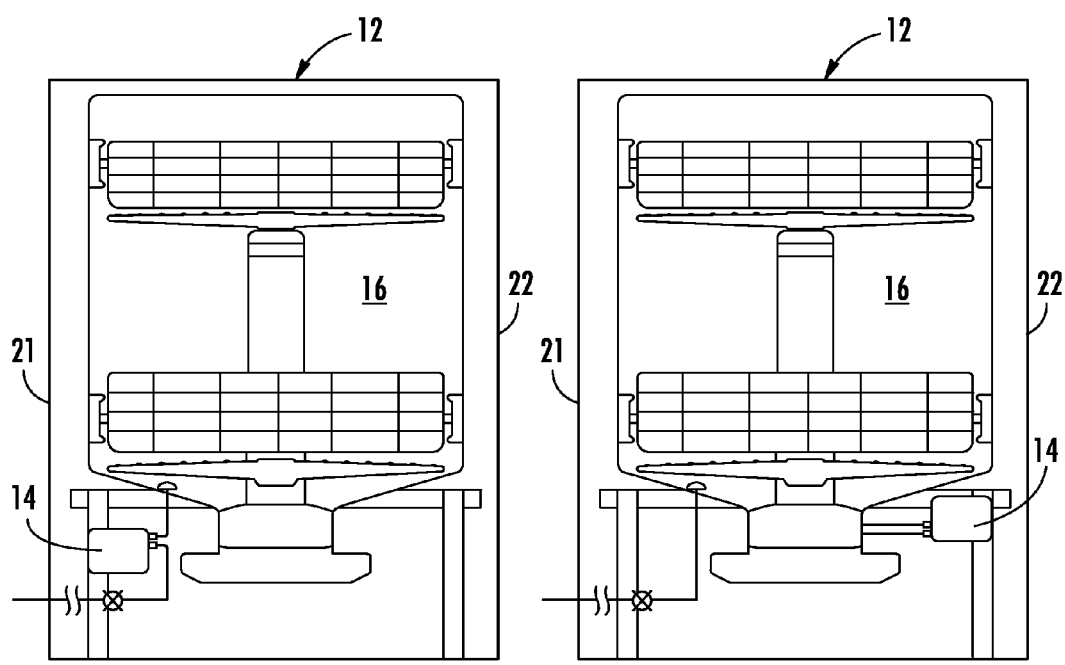
FIG. 4 is a front elevational view of an aspect of the present invention.
FIG. 5 is a front elevational view of another aspect of the present invention.

While in one embodiment the ozone supply module is a removable cartridge, it is also possible that the ozone supply module will be an integrated ozone supply component of the overall appliance and not be removable. However, this is not typically the case. As shown in FIGS. 4-5, the ozone supply module may be in line within the appliance to provide a single dose of ozone (FIG. 4) or tap water can be recirculated through the module 14 and into the tub using a pump that is integral with the ozone supply module 14 to replenish ozone and provide greater amounts of ozonated water into the interior 16 of the appliance 12. For example, as shown in FIG. 5, the ozone supply module 14 with an integrated or associated pump can supply a single dose or repeated doses of ozonated water to treat the interior of the dishwasher (or other appliance), the articles within the dishwasher (or other appliance) and/or anything else spaced within the interior 16 of the appliance; in this manner, the amount of dissolved ozone (and typically hydrogen peroxide and/or hydroxyl radicals, especially when the cartridge includes an aluminosilicate component) can be increased. Additionally, in either of the single dose (FIG. 4) or the multiple dose capable systems (FIG. 5), the appliance may adjust the supply of ozonated fluid (water) to the interior 16 of the appliance based upon the temperature of the water, the timing in the cycle, or both of these factors or other factors when determining when to activate the module and/or the duration of such activation.

Figure 6:
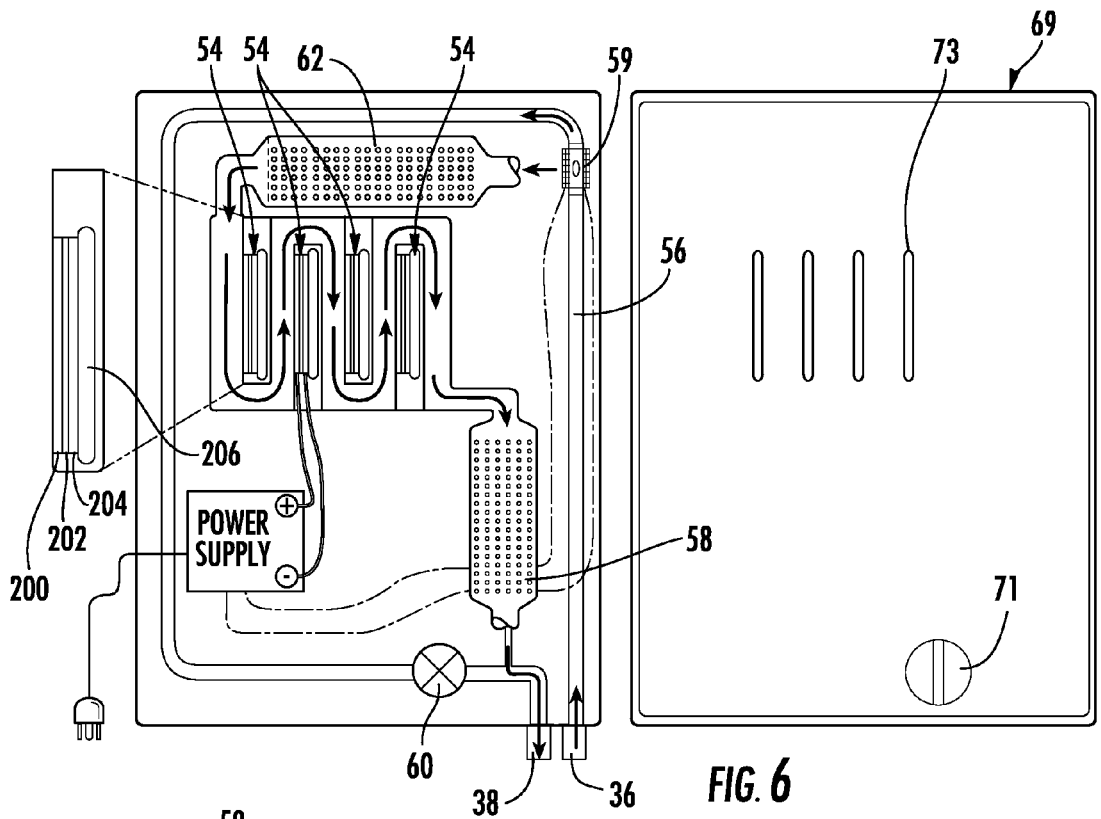
FIG. 6 is a schematic view of an aspect of the present invention (left side) and an associated covering (right side)
Figure 7:
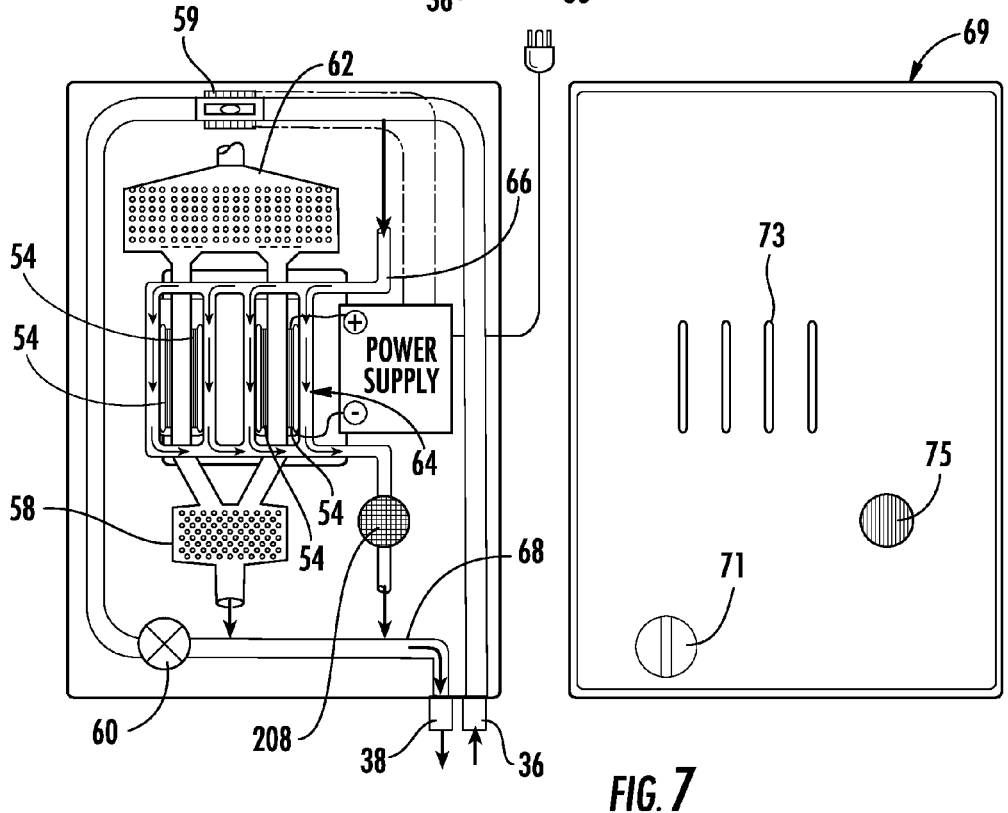
FIG. 7 is a schematic view of another aspect of the present invention (left side) and an associated covering (right side)

Various embodiments of the ozone supply module or individual components thereof are shown in FIGS. 6-13. FIGS. 6 and 7 are a general schematic of the interior of the ozone supply module on the left hand side and a typical cover associated with the module on the right hand side. As shown in FIG. 6, water can enter a water inlet 36 flowing predominantly through the module without treatment; however, at least a portion, typically between about 1 and about 15% by volume of the water received by the water inlet, is passed through the treatment portion of the ozone supply module. A rotational solenoid valve 59 may be used as a by-pass to prevent water from entering the treatment line 57. Up to about 15% by volume of fluid (water) may pass through the treatment portion, more typically up to about 10% by volume and even more typically up to 5% by volume. A portion of the fluid (water) travels through the main fluid (water) line 56 and a portion travels through the fluid (water) treatment line 57 beginning at a first location before merging back into the main fluid (water) line after being treated, typically at a second location within the module.

The ozone supply module treatment portion, which contains the elements that treat or interact with the water traveling through the fluid (water) treatment line 57, typically contains at least one proton exchange membrane cell ozone generator or other ozone generator 54. The proton exchange membrane cell(s) of the ozone supply module may be configured in series or in parallel. Typically, the water to be treated by the ozone generator such as the proton exchange membrane cell(s) departs the main fluid (water) line 56 at a first location typically after the fluid enters the module and is pretreated with by the deionizing resin to remove dissolved metallic ions (particularly bi- and tri-valent metallic ions) that may harm the proton exchange membrane cell(s). Once filtered by the deionizing resin (if present) the filtered water typically passes through the proton exchange membrane cell(s). After the fluid, typically water, is passed through the proton exchange membrane cell(s), the fluid travels further and typically into contact with an aluminosilicate component, which adds peroxide and hydroxyl radicals to the dissolved ozone containing fluid thereby increasing the oxidative potential. The aluminosilicate forms and/or boost hydrogen peroxide and/or hydroxyl radicals in the fluid (for example, water). These components add further functionality to the ozonated fluid (water). As shown in FIGS. 6 and 7, the main fluid (water) travel line 56 typically contains a balancing valve 60 prior to reaching the water outlet 38. The balancing valve operates to throttle the flow of fluid through the main line by adding back pressure to the main water line to ensure proper division of fluid (water) through the treatment line.

The water passing through the treatment portion of the ozone supply module typically does so based upon a combination of the venturi effect, which is the reduction of dynamic fluid pressure that results when a fluid flows through a constricted section of pipe, and the use of inside diameter changes and flow restrictions (flow restriction devices, i.e. balancing valve 60) within the water lines of the module are typically used to drive the flow of water through the treatment portion of the module. Deionizing resin of the module may also be included as a replaceable component within the module itself. Additionally, the deionizing resin portion may be completely removed from the module and not employed.

In addition to the deionizing resin and the proton exchange membrane cell(s), the module may also contain an aluminosilicate component, which is typically ALUSIL™ or ALUSIL NZ™ from Selecto Scientific, Inc. of Suwanee, Ga. The aluminosilicate component is typically an aluminosilicate salt, more typically sodium aluminosilicate. The aluminosilicate component typically includes a combination of a nanoparticulate compound typically chosen from a transition metal oxide, metal hydroxide, or combinations thereof in an aluminosilicate. For example, titanium dioxide or a nanozinc component (engaged) bound to an aluminosilicate using a binder, in particular, a polyvinylpyrollidone. The aluminosilicate typically has an average pore diameter ranging from about 100 to about 300 angstroms or up to about 300 angstroms. The nanoparticulate compound is usually either distributed on or in the aluminosilicate component. The aluminosilicate compound is typically a synthetic aluminosilicate component.

Additionally, an alternative module of the present invention may also solely include the aluminosilicate component, which forms and/or boosts hydrogen peroxide and/or hydroxyl radicals in the fluid (water).

As shown in FIG. 7, the module may include a water cooling subsystem that contains a second alternative path from the main fluid (water) travel line 56. The second water transfer line 66 supplies water to the water cooling subsystem 64, which operates to cool the proton exchange membrane cell(s). The water flowing through the water cooling subsystem 64 rejoins the main fluid (water) line 56. The water from the water cooling subsystem typically rejoins the main fluid (water) line 56 after the water treated by the proton exchange membrane cell(s) rejoins the main fluid (water) travel line. This location is shown as location 68 in FIG. 7.

Figure 8:
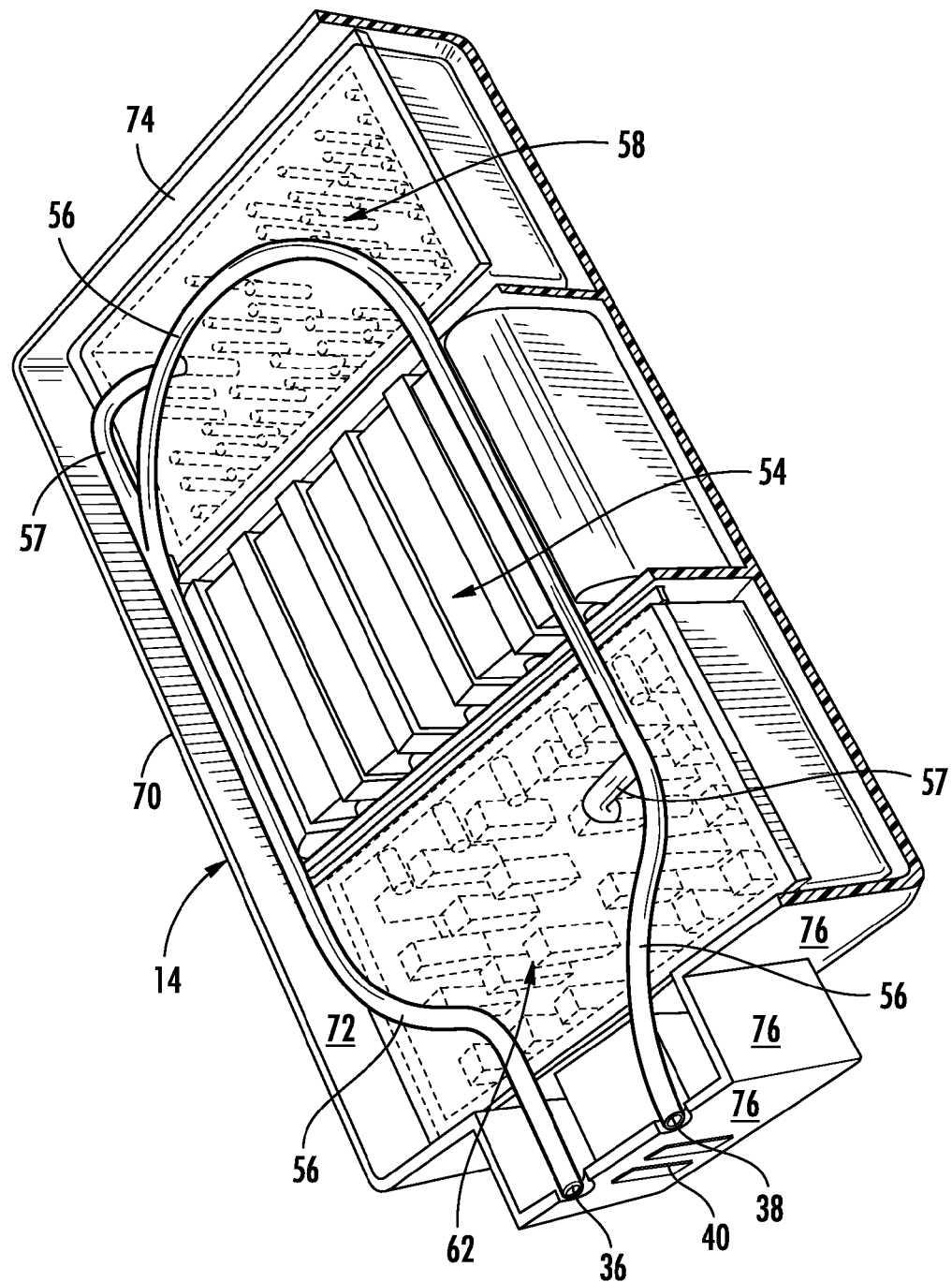
FIG. 8 is a top perspective view of an embodiment of the present invention with the top of the module housing removed.
Figure 9:
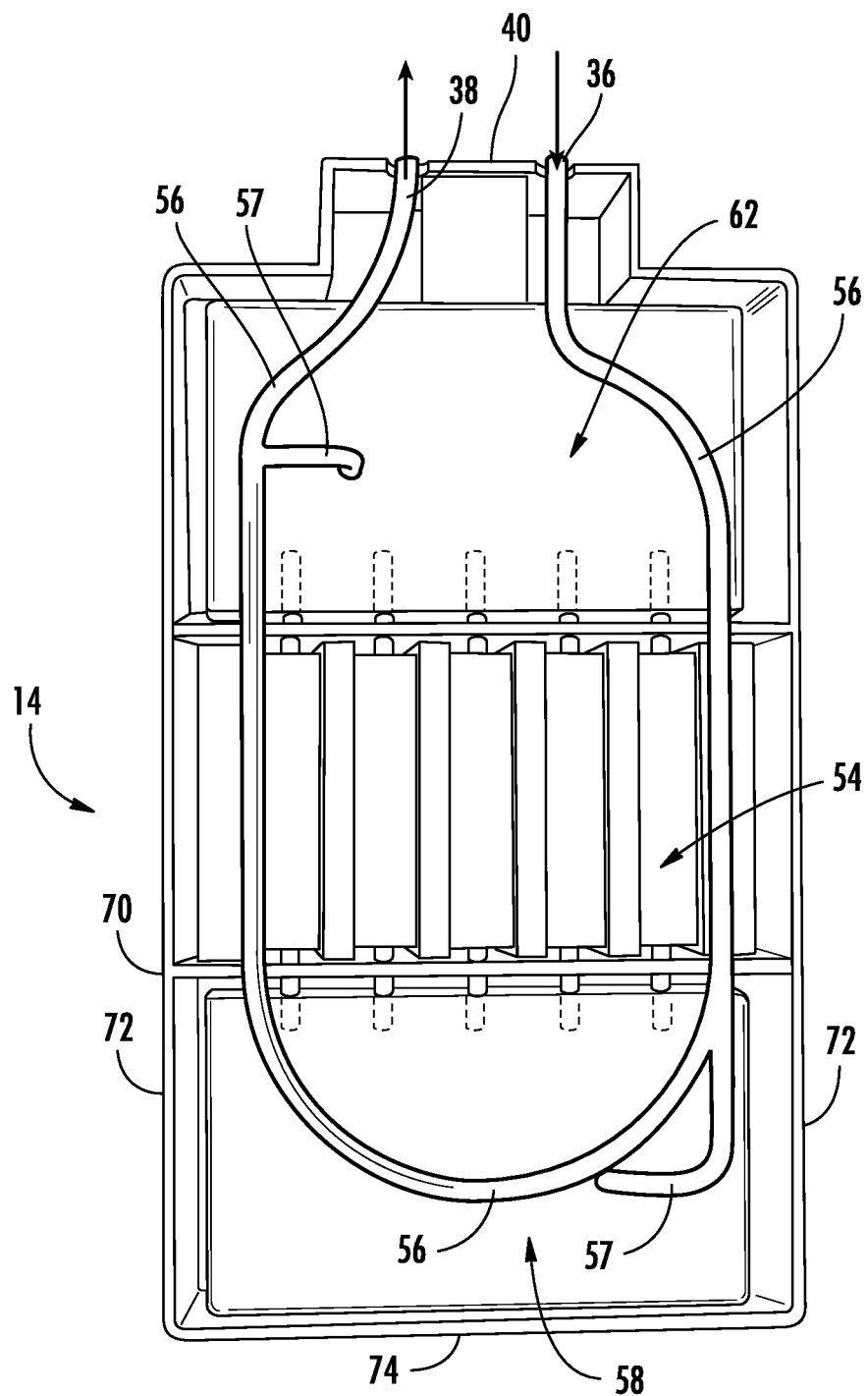
FIG. 9 is a top plan view of an embodiment of the present invention.
Figure 10:
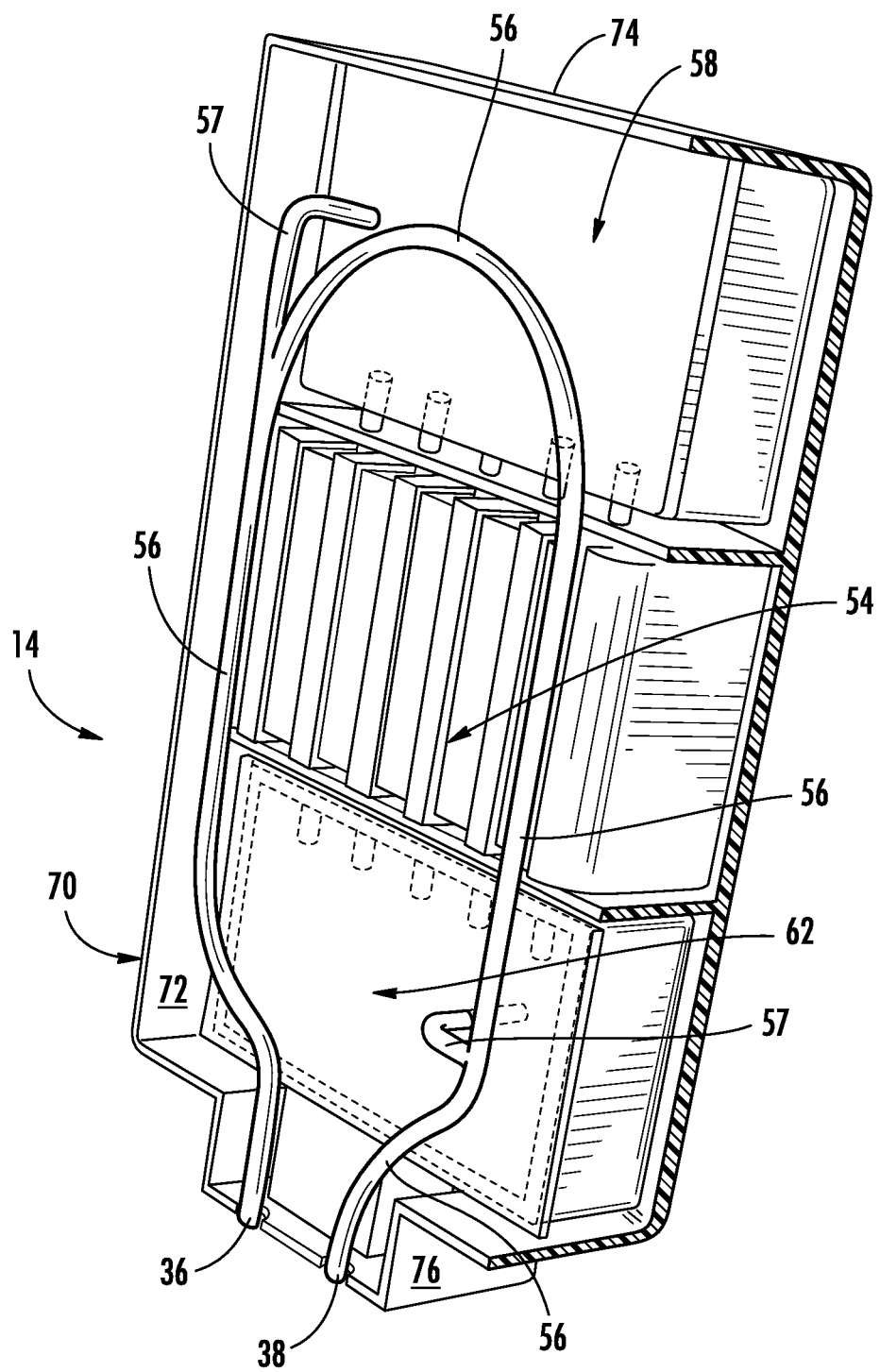
FIG. 10 is a top perspective view of an embodiment of the present invention with the top of the module housing removed.

As shown in FIGS. 8-10, the ozone supply modules 14 typically include a housing 70 that typically encloses the contents of the module and typically has rectangular cross-section, but the cross-section could be any geometric form including cylindrical or oval. The housing 70 typically has a bottom surface (not shown), a top surface (not shown) two side walls 72, a rear wall 74 (the wall typically opposite the water inlet and water outlet and optional electrical connection), and a front wall 76, which is the wall typically containing the water inlet, the water outlet, and the electrical connection when utilized.

As shown in FIGS. 8-10, the deionizing resin and the aluminosilicate component are optional. The proton exchange membrane cell(s) are utilized to form ozonated water and are positioned within the module housing. The main fluid travel line 56 and the water treatment portion 57 are typically also located within the housing 70. Typically, as shown, the housing is generally divided into three separate chambers. One chamber typically contains the deionizing resin, one chamber typically contains the proton exchange membrane cell(s), and one chamber typically contains the aluminosilicate component. Each of these components may individually be contained within a removable housing. The removable sub-housing components may be made to snap into or otherwise securely engage the housing 70 of the module such that the sub-housing components are held within a chamber. For example, a deionizing resin portion may be replaced with a new, subsequent deionizing resin portion of the cartridge when the deionizing resin has lost a majority or all of its functionability or at the desire of the user. In this manner the entire ozone supply module does not need to be disposed of when the deionizing resin has seen its ability to carry out its function substantially decline due to one or more subcomponents of the module.

The electrical connection 40 supplies power to the proton exchange membrane cell(s) 54 via electrical connection contained within the module. The electrical power source may be the appliance 12 or a direct power source from a household power socket or other power supply. The cartridge typically has electrical connection 40 and typically includes two low voltage (from about 1 VDC to about 10 VDC) sliding connectors. These are typically metal connectors that carry the power to the proton exchange membrane cell(s) inside the cartridge.

Figure 11:
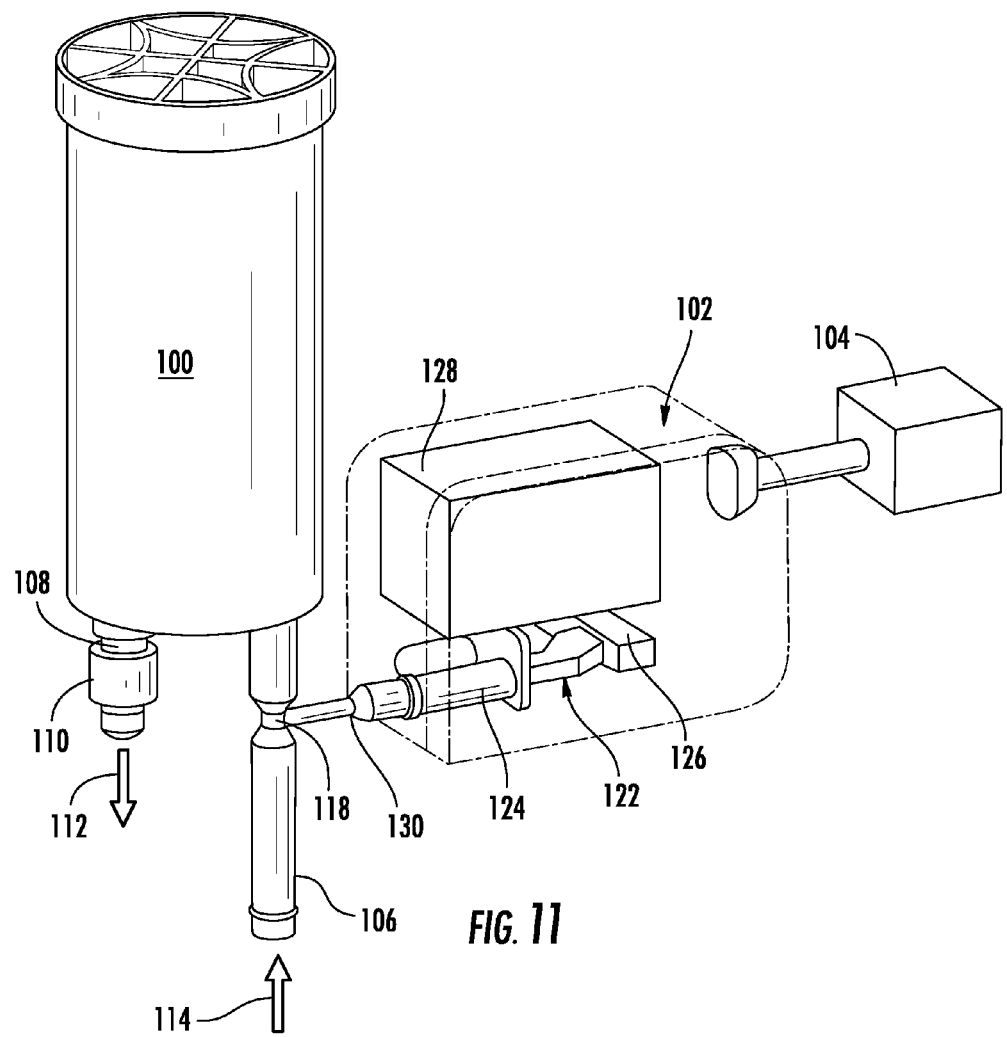
FIG. 11 is a perspective view of another embodiment of the present invention.
Figure 12:
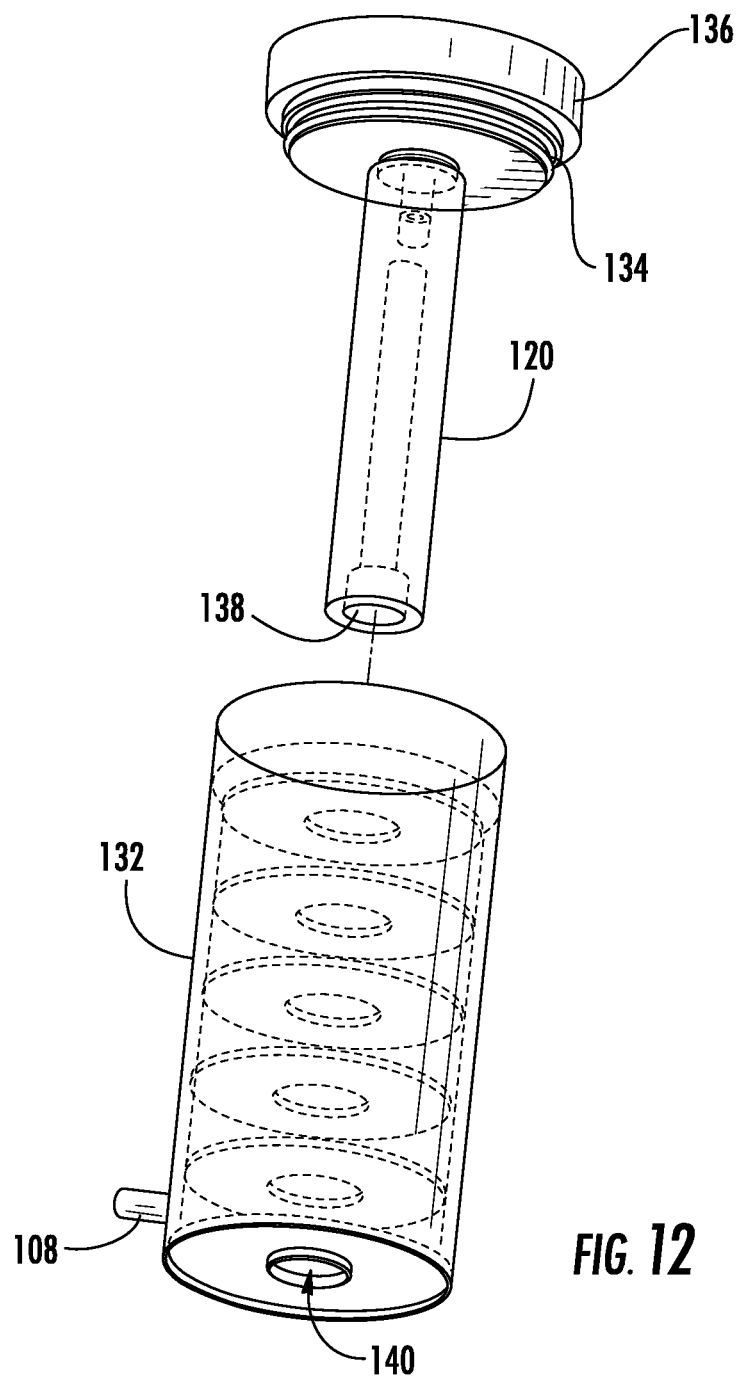
FIG. 12 is an exploded view of another embodiment of a module according to an aspect of the present invention.
Figure 13:
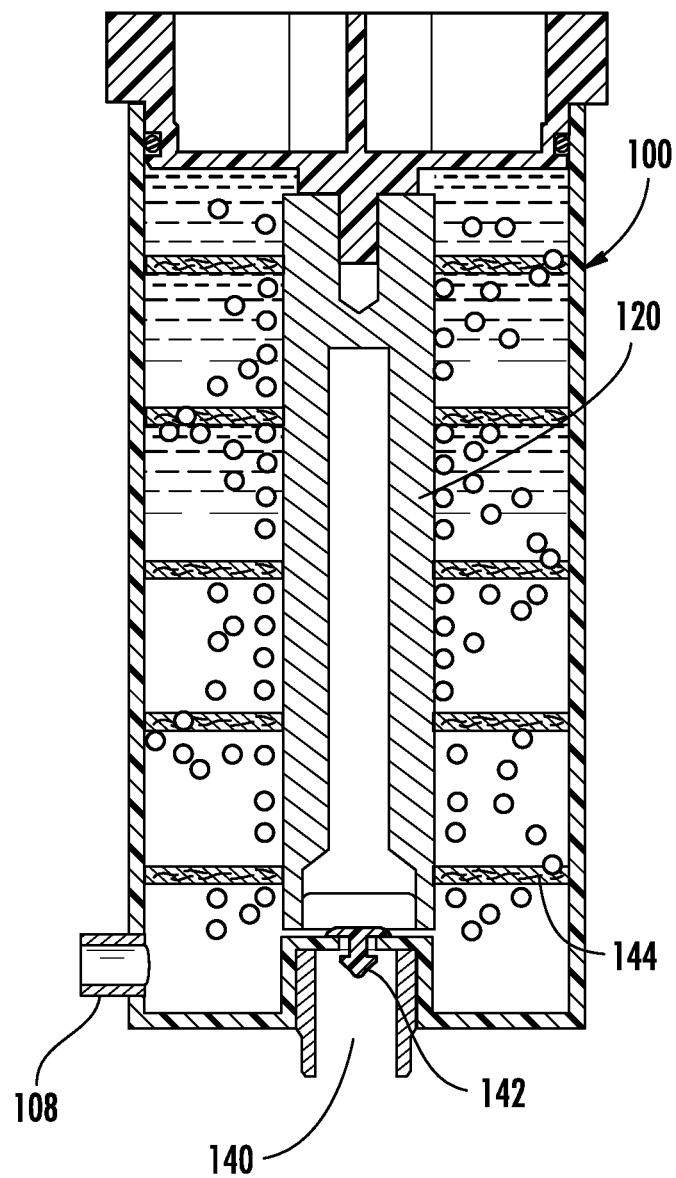
FIG. 13 is an elevated cross-sectional view of another embodiment of the present invention.

According to an alternative embodiment of the present invention, which is shown in FIGS. 11-13, a module 100 may be operably connected to a separate ozone generator 102. As before, the separate ozone generator 102 may be a proton exchange membrane cell(s), as discussed above, which is based on fuel cell technology. The proton exchange membrane cell(s) typically used in connection with the various aspects of the present invention consist of three components, an anode 200, a proton exchange membrane 202, and a cathode 204. The anode and cathode are usually made of a porous metal similar to that used in reusable commercial water filters. The material is typically a 316 stainless steel or titanium, but in a very small quantity. Another approach employs an open mesh for the electrodes. The anode is typically coated with a catalyst, but the cathode is typically bare metal. The proton exchange membrane itself is typically a durable polymer that acts as a solid acid. One such proton exchange membrane is sold under the name NAFION™ by DuPont. The cell is typically assembled by placing the proton exchange membrane between the anode and cathode and applying a clamping or spring compression force to create a pressure of typically about 15 psi or less across the face of the anode. The catalyst is typically a lead oxide catalyst, a tin oxide catalyst or boron doped diamond. In a proton exchange membrane cell, during operation, a portion of the water flowing through the cell is converted by the cell into pure ozone at the anode. The balance of the water that is flowing through the cell picks up the ozone immediately at the point of generation at the anode. The water flows through the anode, which is typically made of porous metal, either a mesh or sintered, and leaves the cell, ready to destroy microorganisms, bacteria and viral components as discussed herein. Typically, water is on the anode. As discussed previously, the use of a deionizing resin can lengthen the life of the proton exchange membrane cell by the removal of dissolved ions. An air venting area 206 allows for venting on the cathode side of the proton exchange membrane cell, including the venting of hydrogen gas and other byproducts of the reaction, to the outside air to prevent hazardous accumulation of components.

A manual switch or valve adjustment is typically located on the outer covering 69, 73 of the cell (see FIGS. 6-7). In the case of the embodiment shown in FIG. 7 employing a water cooling system, a Gortex®-like (a waterproof or breathable fabric), which is a polyvinylpyrollidone material 208 may be used to vent reaction products to the ambient air through a vent port 73 or 75. Vent port 75 is typically a finer mesh screen than the vent ports 73, which are apertures, typically elongated narrow slit apertures, in the outer covering 69 of the module.

Another alternative ozone generator is a corona discharge-type generator. Such a generator is fed two inputs, ambient air and a low voltage direct current. The air is typically pumped into the generator, using an air pump, which is shown as air pump 104 (see FIG. 11). The air flow may be sourced by alternatively shunting a small airflow from a pump or blower that is already used for other functions in an appliance. Typically, the air used should be dried i.e. at a maximum humidity level such that in a non-condensive state, above the dew point. This is also referred to as a non-saturation level for the moisture. If the air is dried, the air is typically dried by passing it through or by a desiccant, typically a chemical such as calcium chloride or other hydroscopic salt (crystals). A replaceable desiccant cartridge may be used. The desiccant may contain a color changing moisture sensitive material to indicate when the desiccant has been exhausted. The dried air reduces the formation of acids from the nitrogen based compounds that are often produced when air is electrolyzed by corona systems to produce ozone. Dry air is also preferred because the generator itself operates at a high voltage, typically between from about 5,000 to about 20,000 DC. If moisture enters the system, it breaks down the air gap that is essential to ozone production. Drier air produces more ozone.

The corona discharge cell typically consists of an assembly of two electrodes and a dielectric barrier. The electrodes generate heat as a bi-product and are often cooled by the incoming air. High output units can have heat dissipating fins on the outside of the electrodes that are cooled by the forced air. The cooling is typically used so as to prevent the destruction of ozone by the heat. One particular corona discharge system that may be used is a cold corona discharge system available from DEL OZONE, Inc. of San Louis Obispo, Calif.

According to an aspect of the present invention, the module 100 may be operably connected to a water inlet or a water source via a water inlet 106. The treated water exits through a fluid (water) outlet 108. Typically, a discharge valve 110 helps regulate discharge of treated fluid (water) 112. In operation, fluid (typically tap water) 114 flows into water inlet 106. The fluid, which is typically water and will be referenced as water throughout the rest of this example, is infused with ozone using the ozone generator that supplies ozone at juncture 118. Thereafter, the water contains a level of dissolved ozone and is ozonated water. The ozonated water typically then flows into the module 110 where it is typically treated by coming into contact with an aluminosilicate component as discussed previously. The aluminosilicate component of FIGS. 11-13 is shown as reference number 120.

The ozone generator 102 typically contains an ozone generating element 122, which is typically a cold plasma corona discharge type unit. The ozone generator 102 typically includes a discharge portion 124 and an advanced plasma gap portion 126 and a power supply 128. Typically, a check valve 130 to prevent back flow is also used, but the check valve is optional and may be omitted. The air pump or other air source (such as venturi suction) pushes air through the ozone generating element 122 such that ozone gas is added at junction 118 to the tap water (or other fluid) travelling into the fluid (water) inlet 106. The ozonated water thereafter contacts the aluminosilicate component within module 100. The aluminosilicate component, as discussed previously, produces hydrogen peroxide and hydroxyl radicals, which further enhance the functionality of the ozonated water to treat, disinfect, or otherwise reduce microbial or viral compounds within an appliance, on an article within an appliance, or on an interior surface of the appliance. Typically, the pressure within the module 100 is at least somewhat higher than the pressure outside the module. Additionally, the aluminosilicate component contained within the module 100 is typically wetted by water. The ozone generator 102 may be a separate replaceable component or, more typically, is integral with the appliance. The ozone generator is typically spaced within the appliance housing. The ozone generator typically delivers ozone gas to the water supply via the venturi effect.

Also, according to another aspect of the present invention, a method of treating an article, an interior surface of an appliance, or a substance within the appliance with the ozonated/treated fluid (water) is provided. The method includes obtaining ozonated water that optionally also contains hydrogen peroxide and/or hydroxyl radicals and contacting the at least ozonated water with an article spaced within a processing chamber of an appliance, into contact with the interior of the appliance, or a fluid within the appliance. The ozonated or otherwise enhanced water/fluid freshens the odor of the fluid, article, or the interior surface of the appliance. Additionally, the ozonated water operates to reduce the microbial and viral count in a fluid that it comes in contact with, an article the ozonated water comes in contact with or the interior surface of the appliance that the ozonated water comes into contact with. In one example, the ozonated water may be applied to clothing spaced within a washer and/or dryer. Yet another example includes the application of the ozonated water to a food product or food product holding chamber within an appliance such as a refrigerator and/or freezer. In another system, the ozonated water may be added to the water of a dishwasher such that the surfaces of the articles within the dishwasher are treated with the ozonated water, the water within the dishwasher is treated, and/or the interior surface of the dishwasher is treated with the ozonated water. The ozonated water operates to sanitize the surface of what it contacts and/or enhance the fresh smell of the appliance or article treated by the ozonated water.

As shown in FIG. 12, the module 100 contains a housing 132, which is shown as circular, but could be of any general shape as design requires. The aluminosilicate component is typically a cylindrical shaped nano-ceramic insert that is replaceable. An o-ring seal 134 on a lid 136 creates an at least substantially or completely water tight seal when the top 136 is engaged to the housing 132. The top 136 is typically removably and securely engaged to the housing 132 by threads in a screw-type fashion that creates a water-tight seal. There is typically an o-ring sealing surface at the bottom of the aluminosilicate component 120 as well.

In an alternative aspect shown in FIG. 13, ozonated air is not injected into the water prior to the water entering the inlet of the module 110, but ozonated water is created by ozone gas entering the module 100 directly through an air inlet 140. The ozone gas activates a valve 142, which is typically an umbrella valve allowing the ozonated air to enter the module. The ozone gas is typically slowed by a plurality of baffles 144 spaced within the housing of the module 100. Typically, the baffles have one aperture or a plurality of apertures on alternative sides such that the ozone bubbles must travel the maximum distance and thus have maximum time to contact the aluminosilicate component while in the module. Once treated, the water entering water inlet 106 leaves via the water outlet 108.

It is to be understood that variations and modifications can be made on the aforementioned structure without departing from the concepts of the present invention, and further it is to be understood that such concepts are intended to be covered by the following claims unless these claims by their language expressly state otherwise.

A. An appliance ozone supply module for supplying ozonated water to a home appliance, more typically a home appliance ozone supply module comprising:

a home appliance module housing comprising a water inlet; a water outlet; and an aluminosilicate component spaced within the module housing such that when the module is engaged to a home appliance the module receives water through the water inlet, water contacts the aluminosilicate compound and the water leaves the module through the water outlet; and wherein the ozone supply module is capable of being removably changed between being engaged and disengaged with the home appliance and wherein ozone supply module produces water to be delivered to a chamber within the home appliance when the module is in the engaged position with the home appliance and the water leaving the module and being delivered to the home appliance chamber comprises hydrogen peroxide.

B. The residential home appliance ozone supply module of any combination of paragraphs or combination of any elements or subcombination of components from A or C-S, wherein the aluminosilicate compound comprises a synthetic aluminosilicate component.

C. The residential home appliance ozone supply module of any combination of paragraphs or combination of any elements or subcombination of components from A-B or D-S, wherein the aluminosilicate component comprises a combination of a nanoparticulate compound chosen from the group consisting a transition metal oxide, metal hydroxides, or combinations thereof and an aluminosilicate wherein the aluminosilicate has an average pore diameter ranging from about 100 to about 300 angstroms and wherein the nanoparticulate compound is either distributed on or in the aluminosilicate.

D. The residential home appliance ozone supply module of any combination of paragraphs or combination of any elements or subcombination of components from A-C or E-S, wherein the water received by the water inlet comprises dissolved ozone and the dissolved ozone contacts the aluminosilicate prior leaving through the water outlet.

E. The residential home appliance ozone supply module of any combination of paragraphs or combination of any elements or subcombination of components from A-D or F-S, wherein the water received by the water inlet comprises dissolved ozone and the dissolved ozone contacts the aluminosilicate prior leaving through the water outlet.

F. The residential home appliance ozone supply module of any combination of paragraphs or combination of any elements or subcombination of components from A-E or G-S, wherein the water received by the water inlet comprises dissolved ozone and the dissolved ozone contacts the aluminosilicate prior leaving through the water outlet.

G. The residential home appliance ozone supply module of any combination of paragraphs or combination of any elements or subcombination of components from A-F or H-S, wherein the water received by the water inlet comprises dissolved ozone and the dissolved ozone contacts the aluminosilicate prior leaving through the water outlet.

H. The residential home appliance ozone supply module of any combination of paragraphs or combination of any elements or subcombination of components from A-G or I-S, wherein the water received by the water inlet comprises tap water and the tap water further comprises at least about 0.3 ppm hydrogen peroxide after contacting the aluminosilicate when leaving through the water outlet.

I. The residential home appliance ozone supply module of any combination of paragraphs or combination of any elements or subcombination of components from A-H or J-S, wherein the tap water comprises from about 0.3 ppm to about 0.8 ppm hydrogen peroxide after contacting the aluminosilicate when leaving through the water outlet.

J. The residential home appliance ozone supply module of any combination of paragraphs or combination of any elements or subcombination of components from A-I or K-S, wherein the module further comprises a plurality of baffles positioned within the module to increase the flow path through module thereby increasing the contact time between the dissolved ozone and slowing the flow rate of the water through the module and wherein the aluminosilicate component is positioned within a porous column.

K. The residential home appliance ozone supply module of any combination of paragraphs or combination of any elements or subcombination of components from A-J or L-S, wherein the porous column extends at least substantially the length of the module and the water inlet and water outlet are both on the bottom of the module and the porous column engages a lid that engages the lid onto the module to securely seal the module.

L. The residential home appliance ozone supply module of any combination of paragraphs or combination of any elements or subcombination of components from A-K or M-S, wherein the porous column extends the length of the module and engages both the lid and the bottom of the module and wherein a valve operably connects the porous column and the bottom of the module such that an ozone supply, when delivered to the porous column travels through the valve, through the aluminosilicate component and into the water contained within the module.

M. The residential home appliance ozone supply module of any combination of paragraphs or combination of any elements or subcombination of components from A-L or N-S, wherein the porous column receives ozonated air and the valve is an umbrella valve.

N. The residential home appliance ozone supply module of any combination of paragraphs or combination of any elements or subcombination of components from A-M or O-S, wherein the interior of the housing is at a higher pressure than the exterior of the housing.

O. The residential home appliance ozone supply module of any combination of paragraphs or combination of any elements or subcombination of components from A-N or P-S, further comprising:

a proton exchange membrane cell; and a water conveying system within the module housing and operably connected to both the water inlet and water outlet and configured to allow water to flow through the proton exchange membrane and into contact with the aluminosilicate compound after passing through the proton exchange membrane;

wherein the module housing further comprises an electrical connector that allows the module to receive electrical power from a home appliance when the module is operably connected to a home appliance and supply electrical power to the proton exchange membrane cell; and wherein the water leaving the module and being delivered to the home appliance chamber comprises hydrogen peroxide and dissolved ozone.

P. The residential home appliance ozone supply module of any combination of paragraphs or combination of any elements or subcombination of components from A-O or Q-S, wherein the water conveying system comprises a main water line and a water treatment line that departs the main water line at a first location and merges with the main water line at a second location wherein the first location is closer to the water inlet along the main water line than the second location.

Q. The residential home appliance ozone supply module of any combination of paragraphs or combination of any elements or subcombination of components from A-P or R-S, wherein from about 85% to 95% by volume of the water volume entering the water inlet travels along the main water line when the module is operably connected to the home appliance and from about 5% to about 15% by volume travel through the water treatment line of the water conveying system.

R. The residential home appliance ozone supply module of any combination of paragraphs or combination of any elements or subcombination of components from A-Q or S, further comprising a deionizing resin water filtration component capable of removing dissolved metallic ions from water passing through the deionizing resin water filtration component and the deionizing resin water filtration component is spaced within the module housing and wherein the water conveying system is configured to pass water flowing through the water inlet through the deionizing resin water filtration component prior to passing through the proton exchange membrane and passed through or into contact with the aluminosilicate component thereafter.

S. The residential home appliance ozone supply module of any combination of paragraphs or combination of any elements or subcombination of components from A-R, further comprising a deionizing resin water filtration component capable of removing dissolved metallic ions from water passing through the deionizing resin water filtration component and the deionizing resin water filtration component is spaced within the module housing and wherein the water conveying system is configured to pass water flowing through the water inlet and the water conveying system through the deionizing resin water filtration component prior to passing through the proton exchange membrane and passed through or into contact with the aluminosilicate component thereafter.

T. An ozone supply module for supplying ozone to a residential appliance comprising:

a module housing comprising:
a water inlet;
a water outlet;
at least one electrical connection that supplies power to the ozone supply module when the ozone supply module is operably connected to a home appliance;
an aluminosilicate component spaced within the module housing;
a deionizing resin positioned within the housing;
a proton exchange membrane cell positioned within the housing that generates ozone; and
a water conveying system within the module housing and operably connected to both the water inlet and water outlet and configured to allow water to flow through the deionizing resin, thereafter, the proton exchange membrane and thereafter into contact with the aluminosilicate compound; and wherein, when the module is engaged to a home appliance, the module receives water through the water inlet, water contacts the aluminosilicate compound capable of adding hydrogen peroxide to water and the water leaves the module through the water outlet; and wherein the ozone supply module is configured to be removably engaged and disengaged with the home appliance and wherein the ozone supply module produces water to be delivered to a chamber within the home appliance when the module is in the engaged position with the home appliance and the water leaving the module and being delivered to the home appliance chamber comprises: dissolved ozone and hydrogen peroxide.

U. The ozone supply module of any combination of paragraphs or combination of any elements or subcombination of components from T or V, wherein the water conveying system comprises a main water line and a water treatment line that departs the main water line at a first location and merges with the main water line at a second location wherein the first location is closer to the water inlet along the main water line than the second location.

V. The ozone supply module of any combination of paragraphs or combination of any elements or subcombination of components from T-U, wherein from about 85% to 95% by volume of the water volume entering the water inlet travels along the main water line when the module is operably connected to the home appliance and from about 5% to about 15% by volume travel through the water treatment line of the water conveying system and the water treatment line travels to the deionizing resin, the proton exchange membrane and the aluminosilicate component and wherein the ozone supply module comprises at least two voltage sliding connectors, typically sliding connectors, delivering from about 1 volt of direct current to about 10 volts of direct current to the ozone supply module.

W. An ozone supply module comprising:

a housing comprising an interior surface, a water inlet, a water outlet, a base and a lid having an ozone inlet;

an aluminosilicate compound positioned within a porous plastic tube within the housing and capable of enhancing the level of hydroxyl radicals in water containing ozone when the water containing ozone contacts the aluminosilicate compound; and at least one baffle capable of slowing the water flow through the ozone supply module wherein the baffles comprise at least one aperture and a perimeter and the porous plastic tube is spaced within the aperture such that the baffle is positioned around the porous plastic tube and within the housing such that the perimeter of the baffle at least substantially abuts the interior surface of the housing.

X. The ozone supply module of any combination of paragraphs or combination of any elements or subcombination of components from W, wherein the aluminosilicate component is capable of producing hydrogen peroxide upon contact with water and comprises a combination of a nanoparticulate compound chosen from the group consisting a transition metal oxide, metal hydroxides, or combinations thereof and an aluminosilicate wherein the aluminosilicate has an average pore diameter ranging from about 100 to about 300 angstroms and wherein the nanoparticulate compound is either distributed on or in the aluminosilicate and wherein ozone is received by the ozone supply module through the ozone inlet in the base of the ozone supply module that includes an umbrella valve to seal the porous plastic tube when the porous plastic tube is not receiving ozonated air or ozonated water.

Y. An appliance system comprising:
an appliance having a processing chamber and a module connection;
a removable ozone supply module capable of being engaged and disengaged with the appliance connection comprising:
a housing having an interior, a water inlet, and a water outlet; and
an aluminosilicate component spaced within the interior of the module housing; and
wherein when the module is engaged to the appliance the module receives water through the water inlet, water contacts the aluminosilicate compound and the water leaves the module through the water outlet; and
wherein the ozone supply module produces water to be delivered to the processing chamber within the appliance when the module is engaged with the appliance and the water leaving the module and being delivered to the appliance chamber comprises hydrogen peroxide.

Z. The appliance system of any combination of paragraphs or combination of any elements or subcombination of components from Y or AA-AM, wherein the appliance is a residential appliance chosen from the group consisting of a residential refrigerator, a residential freezer, a residential refrigerator and freezer appliance, a residential laundry washing machine, a residential laundry drying machine, a residential dishwasher, and a residential ice maker.

AA. The appliance system of any combination of paragraphs or combination of any elements or subcombination of components from Y-Z or AB-AM, wherein the appliance system further comprises a recirculation pump that is operably connected to the removable ozone supply module and the processing chamber of the appliance such that the recirculation pump is capable of moving water from the processing chamber of the appliance and through the removable ozone supply module and the water is delivered back to the processing chamber of the appliance.

AB. The appliance system of any combination of paragraphs or combination of any elements or subcombination of components from Y-AA or AC-AM further comprising an ozone generator.

AC. The appliance system of any combination of paragraphs or combination of any elements or subcombination of components from Y-AB or AD-AM, wherein the ozone generator is positioned within the module housing and comprises a proton exchange membrane cell; and
wherein the module comprises at least one electrical contact and electrical connections from the electrical contact to the proton exchange membrane cell to supply electrical power to the proton exchange membrane cell when the module is operably connected to the appliance;
and a water conveying system within the module housing and operably connected to both the water inlet and water outlet and configured to allow water to flow through the proton exchange membrane cell and into contact with the aluminosilicate compound after passing through the proton exchange membrane cell.

AD. The appliance system of any combination of paragraphs or combination of any elements or subcombination of components from Y-AC or AE-AM, wherein the module further comprises a deionizing resin that receives water from the water inlet and delivers water to the proton exchange membrane cell.

AE. The appliance system of any combination of paragraphs or combination of any elements or subcombination of components from Y-AD or AF-AM, wherein the water conveying system comprises a main water line and a water treatment line that departs the main water line at a first location and merges with the main water line at a second location wherein the first location is closer to the water inlet along the main water line than the second location.

AF. The appliance system of any combination of paragraphs or combination of any elements or subcombination of components from Y-AE or AG-AM, wherein from about 85% to 95% by volume of the water volume entering the water inlet travels along the main water line when the module is operably connected to the home appliance and from about 5% to about 15% by volume travel through the water treatment line of the water conveying system.

AG. The appliance system of any combination of paragraphs or combination of any elements or subcombination of components from Y-AF or AH-AM, wherein the ozone generator is outside of the module housing.

AH. The appliance system of any combination of paragraphs or combination of any elements or subcombination of components from Y-AG or AI-AM, wherein the appliance comprises a housing and the appliance comprises the ozone generator and the ozone generator is integral with the appliance within the appliance housing.

AI. The appliance system of any combination of paragraphs or combination of any elements or subcombination of components from Y-AH or AJ-AM, wherein the ozone generator comprises an ozone generator chosen from the group consisting of a proton exchange membrane cell and a cold corona discharge generator.

AJ. The appliance system of any combination of paragraphs or combination of any elements or subcombination of components from Y-AI or AK-AM, wherein the ozone generator comprises a cold corona discharge generator.

AK. The appliance system of any combination of paragraphs or combination of any elements or subcombination of components from Y-AJ or AL-AM, wherein the ozone generator delivers ozone gas to a water supply to produce ozonated water and wherein the module receives the ozonated water via the water inlet.

AL. The appliance system of any combination of paragraphs or combination of any elements or subcombination of components from Y-AK or AM, wherein the ozone generator delivers ozone gas to the water supply via a venturi effect and the interior volume of the module is at a higher pressure than the pressure outside the module.

AM. The appliance system of any combination of paragraphs or combination of any elements or subcombination of components from Y-AL, wherein the ozone generator further comprises a check valve capable of preventing back flow of water into the ozone generator.

AN. A method of treating an article, an interior surface of an appliance, or a substance within the appliance with an ozonated fluid comprising:

providing: an appliance having a processing chamber and a module connection location and a water supply line that supplies source water;
    a removable ozone supply module capable of being engaged and disengaged with the appliance connection comprising:
    a housing having a water inlet and a water outlet;
    an aluminosilicate component;
    an ozone generator;
    engaging the module with the appliance;
    adding ozone to the source water using the ozone generator to create ozonated water;
    passing the ozonated water through the module via the water inlet such that the ozonated water comes into contact with the aluminosilicate component and leaves the module through the water outlet as enhanced ozonated water that comprises hydrogen peroxide; and
    contacting the enhanced ozonated water leaving the module with at least one article within the processing chamber of the appliance.

AO. The method of any combination of paragraphs or combination of any elements or subcombination of components from AP-AQ, wherein the substance contained within the appliance is a fluid and the enhanced ozonated water reduces microbial count, viral count, or microbial and viral count associated with at least one of the fluid, the article, and the interior surface of the appliance and the appliance is a dishwasher.

AP. The method of any combination of paragraphs or combination of any elements or subcombination of components from AO or AQ, wherein the substance contained within the appliance is a fluid and the enhanced ozonated water freshens the odor of at least one of the fluid, the article and the interior surface of the appliance.

AQ. The method of any combination of paragraphs or combination of any elements or subcombination of components from AO-AP, wherein the ozone generator is spaced within the module and the aluminosilicate component comprises a combination of a nanoparticulate compound chosen from the group consisting a transition metal oxide, metal hydroxides, or combinations thereof and an aluminosilicate wherein the aluminosilicate has an average pore diameter ranging from about 100 to about 300 angstroms and wherein the nanoparticulate compound is either distributed on or in the aluminosilicate.

AR. An appliance system comprising:
    an appliance having an article processing chamber and a module connection;
    a removable ozone supply module capable of being engaged and disengaged with the module connection comprising:
    a housing having a water inlet and a water outlet;
    at least one electrical connection that receives power from the appliance and supplies power to the ozone supply module when the ozone supply module is operably connected to the appliance;
    an aluminosilicate component within the module housing;
    a deionizing resin within the housing;
    a proton exchange membrane cell within the housing that generates ozone and receives electrical power through the at least one electrical connection; and
    a water conveying system within the module housing and operably connected to both the water inlet and water outlet and configured to allow water to flow through the deionizing resin, thereafter, the proton exchange membrane cell and thereafter into contact with the aluminosilicate compound and deliver enhanced ozonated water to the article processing chamber and wherein the enhanced ozonated water comprises hydrogen peroxide.

AS. An ozone supply module for supplying ozonated water to an appliance comprising:
    an appliance module housing comprising: a water inlet; a water outlet; and an electrical connection for receiving electrical power;
    a proton exchange membrane cell positioned within the housing; and
    a water conveying system within the module housing and operably connected to both the water inlet and water outlet and configured to allow water to flow through the deionizing resin and into contact with the proton exchange membrane cell wherein the electrical connector allows the module to receive electrical power from a home appliance when the module is operably connected to a home appliance and supply electrical power to the proton exchange membrane cell and wherein the ozone supply module is capable of being removably changed between being engaged and disengaged with the home appliance and wherein ozone supply module produces water to be delivered to a chamber within the home appliance when the module is in the engaged position with the home appliance and the water leaving the module and being delivered to the home appliance chamber comprises dissolved ozone.

AT. The ozone supply module for supplying ozonated water to an appliance of any combination of paragraphs or combination of any elements or subcombination of components from AS or AU-BE, wherein the module further comprises a deionizing resin position within the module.

AU. The ozone supply module for supplying ozonated water to an appliance of any combination of paragraphs or combination of any elements or subcombination of components from AS-AT or AV-BE, wherein the deionizing resin is contained within a separate deionizing resin housing.

AV. The ozone supply module for supplying ozonated water to an appliance of any combination of paragraphs or combination of any elements or subcombination of components from AS-AU or AW-BE, wherein the deionizing resin housing is removably positioned within the module housing.

AW. The ozone supply module for supplying ozonated water to an appliance of any combination of paragraphs or combination of any elements or subcombination of components from AS-AV or AX-BE, wherein the module comprises a plurality of separate proton exchange membrane cells and wherein the module further comprises an aluminosilicate component spaced within the module housing such that when the module is engaged to a home appliance the module receives water through the water inlet, water contacts the aluminosilicate compound and the water leaves the module through the water outlet; and
    wherein the ozone supply module is capable of being removably changed between being engaged and disengaged with the home appliance and wherein the ozone supply module produces water to be delivered to a chamber within the home appliance when the module is in the engaged position with the home appliance and the water leaving the module and being delivered to the home appliance chamber comprises a peroxide.

AX. The ozone supply module of any combination of paragraphs or combination of any elements or subcombination of components from AS-AW or AY-BE, wherein the aluminosilicate compound comprises a synthetic aluminosilicate component.

AY. The ozone supply module of any combination of paragraphs or combination of any elements or subcombination of components from AS-AX or AZ-BE, wherein the aluminosilicate component comprises a combination of a nanoparticulate compound chosen from the group consisting a transition metal oxide, metal hydroxides, or combinations thereof and an aluminosilicate wherein the aluminosilicate has an average pore diameter ranging from about 100 to about 300 angstroms and wherein the nanoparticulate compound is either distributed on or in the aluminosilicate.

AZ. The ozone supply module of any combination of paragraphs or combination of any elements or subcombination of components from AS-AY or BA-BE, wherein the water conveying system comprises a main water line and a water treatment line that departs the main water line at a first location and merges with the main water line at a second location wherein the first location is closer to the water inlet along the main water line than the second location.

BA. The ozone supply module of any combination of paragraphs or combination of any elements or subcombination of components from AS-AZ or BB-BE, wherein from about 85% to 95% by volume of the water volume entering the water inlet travels along the main water line when the module is operably connected to the home appliance and from about 5% to about 15% by volume travel through the water treatment line of the water conveying system.

BB. The ozone supply module of any combination of paragraphs or combination of any elements or subcombination of components from AS-BA or BC-BE, wherein deionizing resin is a deionizing resin water filtration component capable of removing hardened particles from water passing through the deionizing resin water filtration component and the deionizing resin water filtration component is configured to pass water flowing through the water inlet through the deionizing resin water filtration component prior to passing through the proton exchange membrane and passed through or into contact with the aluminosilicate component thereafter.

BC. The ozone supply module of any combination of paragraphs or combination of any elements or subcombination of components from AS-BB or BD-BE, wherein the water received by the water inlet comprises tap water.

BD. The ozone supply module of any combination of paragraphs or combination of any elements or subcombination of components from AS-BC or BE, wherein the water received by the water inlet comprises tap water.

BE. The ozone supply module of any combination of paragraphs or combination of any elements or subcombination of components from AS-BD, wherein the water received by the water inlet comprises, tap water, the water received by the proton exchange resin comprises filtered water, the water received by the aluminosilicate comprises ozonated water and the water leaving through the water inlet comprises dissolved ozone, hydrogen peroxide and hydroxyl radicals.

BF. An ozone supply module for supplying ozonated water to an appliance comprising:
an appliance module housing comprising: a water inlet; a water outlet; and an electrical connection for receiving electrical power; a proton exchange membrane cell positioned within the housing; and a water conveying system within the module housing and operably connected to both the water inlet and the water outlet and configured to allow water to flow into contact with the proton exchange membrane cell; and
wherein the electrical connection allows the module to receive electrical power from a home appliance when the module is operably connected to the home appliance and supply electrical power to the proton exchange membrane cell and wherein the ozone supply module is capable of being removably changed between being engaged and disengaged with the home appliance and wherein the ozone supply module produces water to be delivered to a chamber within the home appliance when the module is in the engaged position with the home appliance and the water leaving the module and being delivered to the chamber comprises dissolved ozone.

BG. The ozone supply module for supplying ozonated water to an appliance of any combination of paragraphs or combination of any elements or subcombination of components from BF, further comprising a deionizing resin positioned within the appliance module housing and wherein the water conveying system within the appliance module housing and operably connected to the water inlet and the water outlet is configured to allow water to flow through the deionizing resin that is capable of removing hardened particles from water and thereby filter the water flowing therethrough prior to the water flowing into contact with the proton exchange membrane cell.

What is claimed is:

1. An ozone supply module for supplying ozonated water to an appliance comprising:
an appliance module housing comprising: a water inlet; a water outlet; and an electrical connection for receiving electrical power;
a proton exchange membrane cell positioned within the appliance module housing; and
a water conveying system within the appliance module housing and operably connected to both the water inlet and water outlet and configured to allow water to flow into contact with the proton exchange membrane cell and wherein the electrical connection allows the ozone supply module to receive electrical power from an appliance when the ozone supply module is operably connected to an appliance and supply electrical power to the proton exchange membrane cell and wherein the ozone supply module is capable of being removably changed between being engaged and disengaged with the appliance and wherein ozone supply module produces ozonated water to be delivered to an article processing chamber within the appliance when the ozone supply module is in an engaged position with the appliance and the ozonated water leaving the ozone supply module and being delivered to the article processing chamber; and
wherein the ozone supply module is configured to be removably changed between being engaged and disengaged with the appliance, and wherein the ozone supply module further comprises a deionizing resin operable to remove dissolved metallic ions positioned within the ozone supply module.

2. The ozone supply module for supplying ozonated water to an appliance of claim 1, wherein the deionizing resin is contained within a separate deionizing resin housing.

3. The ozone supply module for supplying ozonated water to an appliance of claim 2, wherein the deionizing resin housing is configured to be removably engaged and disengaged from its position within the appliance module housing.

4. The ozone supply module for supplying ozonated water to an appliance of claim 1, wherein the module comprises a plurality of separate proton exchange membrane cells spaced within the module housing such that when the module is engaged to the appliance the module receives water through the water inlet and the water leaves the module through the water outlet; and
wherein the ozone supply module is capable of being removably changed between being engaged and disengaged with the appliance and wherein the ozone supply module produces water to be delivered to a chamber within the appliance when the module is in the engaged position with the appliance and the ozonated water leaving the module and being delivered to the chamber comprises a dissolved ozone.

5. The ozone supply module for supplying ozonated water to an appliance of claim 4, wherein the water conveying system comprises a main water line and a water treatment line that departs the main water line at a first location and merges with the main water line at a second location wherein the first location is closer to the water inlet along the main water line than the second location.

6. The ozone supply module for supplying ozonated water to an appliance of claim 1, wherein the water conveying system comprises a main water line and a water treatment line that departs the main water line at a first location and merges with the main water line at a second location wherein the first location is closer to the water inlet along the main water line than the second location.

7. The ozone supply module for supplying ozonated water to an appliance of claim 6, wherein up to about 85% by volume of the water entering the water inlet travels along the main water line when the module is operably connected to the appliance and up to about 15% by volume travel through the water treatment line of the water conveying system.

8. The ozone supply module for supplying ozonated water to an appliance of claim 5, wherein up to about 85% by volume of the water entering the water inlet travels along the main water line when the module is operably connected to the appliance and up to about 15% by volume travel through the water treatment line of the water conveying system.

9. The ozone supply module for supplying ozonated water to an appliance of claim 8, further comprising a deionizing resin and wherein deionizing resin is a deionizing water filtration component capable of removing dissolved metallic ions from water passing through the deionizing resin water filtration component and the deionizing resin water filtration component is configured to pass water flowing through the water inlet through the deionizing resin water filtration component to form filtered water prior to the filtered water passing through the proton exchange membrane.

10. The ozone supply module for supplying ozonated water to an appliance of claim 9, wherein the water received by the water inlet comprises tap water, and wherein the appliance module housing includes an aluminosilicate component having at least one of titanium dioxide and zinc oxide is positioned within the appliance module housing and configured to contact the ozonated water and produce hydrogen peroxide and hydroxyl radicals prior to the ozonated water leaving the water outlet, and wherein the tap water includes at least about 0.3 ppm hydrogen peroxide after contacting the aluminosilicate component when leaving through the water outlet.

11. The ozone supply module for supplying ozonated water to an appliance of claim 1, wherein the water received by the water inlet comprises tap water and wherein the appliance module housing further comprises an aluminosilicate compound that is a combination of a nanoparticulate compound chosen from a group consisting of a transition metal oxide, metal hydroxides, or combinations thereof and an aluminosilicate wherein the aluminosilicate has an average pore diameter ranging from about 100 to about 300 angstroms and wherein the nanoparticulate compound is either distributed on or in the aluminosilicate and wherein the aluminosilicate compound is configured to contact the ozonated water produced by the proton exchange membrane cell.

12. An appliance system comprising:
an appliance having a processing chamber and a module connection; and
a removable ozone supply module capable of being removably engaged and disengaged with the module connection comprising:
an ozone supply module housing having an interior, a water inlet, a water outlet;
an electrical connection;
a proton exchange membrane cell positioned within the housing and operably connected to the electrical connection; and
a water conveying system within the housing and operably connected to both the water inlet and the water outlet and configured to allow water to flow into contact with the proton exchange membrane cell such that the proton exchange membrane cell generates ozonated water; and
wherein when the ozone supply module is engaged to the appliance the module receives electrical power from the appliance and water through the water inlet, the water contacts the proton exchange membrane cell and the ozonated water leaves the module through the water outlet;
wherein the ozone supply module produces the ozonated water to be delivered to the processing chamber within the appliance when the module is engaged with the appliance and the water leaving the module and being delivered to an appliance chamber comprises dissolved ozone; and
wherein when the ozone supply module is engaged to the appliance, the ozone supply module receives water through the water inlet and the water leaves the module through the water outlet and wherein the water leaving the module and being delivered to the processing chamber comprises dissolved ozone, and wherein the module includes an aluminosilicate component having at least one of titanium dioxide and zinc oxide within the module and is configured to receive ozonated water.

13. The appliance system of claim 12, wherein the appliance is a residential appliance and wherein the removable ozone supply module receives water through the appliance when the ozone supply module is operably connected to the appliance at the module connection and the module further comprises a deionizing resin filter configured to filter dissolved metal ions from water and further configured to pass water flowing through the water inlet and through the deionizing resin filter to produce deionized water prior to the deionized water passing through the proton exchange membrane cell.

14. The appliance system of claim 12, further comprising a second ozone supply module wherein the second ozone supply module is configured to be removably engaged and disengaged with the appliance and wherein the appliance system further comprises a replacement deionizing resin filter and wherein the deionizing resin filter and replacement deionizing filter each comprise a filter housing and each are configured to be removably changed between being engaged and disengaged with the interior of the ozone supply module housing.

15. The appliance system of claim 12, wherein the appliance is a residential appliance chosen from group consisting of a residential refrigerator, a residential freezer, a residential refrigerator and freezer appliance, a residential laundry washing machine, a residential laundry drying machine, a drinking water dispenser appliance, a water heater and a residential dishwasher.

16. The appliance system of claim 15, wherein the appliance system further comprises a recirculation pump that is operably connected to the removable ozone supply module and the processing chamber of the appliance such that the recirculation pump pumps water from the processing chamber of the appliance and through the removable ozone supply module and the water is delivered back to the processing chamber of the appliance and the processing chamber of the appliance is configured to receive an article to be processed by the appliance.

17. The appliance system of claim 12, wherein the water conveying system comprises a main water line and a water treatment line that departs the main water line at a first location and merges with the main water line at a second location wherein the first location is closer to the water inlet along the main water line than the second location and wherein up to about 85% by volume of the water entering the water inlet travels along the main water line when the module is operably connected to the appliance and up to about 15% by volume travel through the water treatment line of the water conveying system.

18. The appliance system of claim 12, wherein the module comprises a plurality of separate proton exchange membrane cells.

\* \* \* \* \*